US009939394B2

(12) United States Patent
Beuth, Jr. et al.

(10) Patent No.: US 9,939,394 B2
(45) Date of Patent: *Apr. 10, 2018

(54) PROCESS MAPPING OF COOLING RATES AND THERMAL GRADIENTS

(71) Applicants: Carnegie Mellon University, Pittsburgh, PA (US); Wright State University, Dayton, OH (US)

(72) Inventors: Jack Lee Beuth, Jr., Pittsburgh, PA (US); Nathan W. Klingbeil, Beavercreek, OH (US); Joy Davis Gockel, Dayton, OH (US)

(73) Assignees: Carnegie Mellon University, Pittsburgh, PA (US); Wright State University, Dayton, OH (US)

(*) Notice: Subject to any disclaimer, the term of this patent is extended or adjusted under 35 U.S.C. 154(b) by 349 days.

This patent is subject to a terminal disclaimer.

(21) Appl. No.: 14/422,092

(22) PCT Filed: Aug. 16, 2013

(86) PCT No.: PCT/US2013/055422
§ 371 (c)(1),
(2) Date: Feb. 17, 2015

(87) PCT Pub. No.: WO2014/028879
PCT Pub. Date: Feb. 20, 2014

(65) Prior Publication Data
US 2015/0219572 A1    Aug. 6, 2015

Related U.S. Application Data

(60) Provisional application No. 61/742,734, filed on Aug. 17, 2012.

(51) Int. Cl.
G01B 21/28    (2006.01)
G01N 25/00    (2006.01)
(Continued)

(52) U.S. Cl.
CPC ............ *G01N 25/00* (2013.01); *B22F 3/1055* (2013.01); *B29C 67/0088* (2013.01);
(Continued)

(58) Field of Classification Search
CPC ............ B29C 67/0055; B29C 67/0085; B29C 37/005; B29C 2037/90; G01B 21/38
(Continued)

(56) References Cited

U.S. PATENT DOCUMENTS

| 6,791,057 B1 | 9/2004 | Kratzsch et al. |
| 6,813,533 B1 * | 11/2004 | Semak .............. B23K 26/34 148/97 |
| 2009/0206065 A1 * | 8/2009 | Kruth .............. B22F 3/1055 219/121.66 |

FOREIGN PATENT DOCUMENTS

| KR | 10-2009-0124939 | 12/2009 |
| WO | WO1995/11100 | 4/1995 |
| WO | WO2014/028879 | 2/2014 |

OTHER PUBLICATIONS

Notification of Transmittal of International Search Report and Written Opinion for corresponding Application No. PCT/US2013/055422, dated Dec. 19, 2013, pp. 1-9.
(Continued)

Primary Examiner — Mohamed Charioui
(74) Attorney, Agent, or Firm — Fish & Richardson P.C.

(57) ABSTRACT

A method performed by one or more processing devices includes conducting a plurality of tests of a manufacturing process. Each test is conducted at a different combination of at least a first process variable and a second process variable, and each test comprises locally heating a region of a structure, where the local heating results in formation of a thermal field in the structure, and assessing a temperature derivative of the thermal field. Based on results of the plurality of tests, a process map of the temperature deriva-
(Continued)

tive of the thermal field is generated, with the temperature derivative based on a function of the first process variable and the second process variable.

24 Claims, 13 Drawing Sheets

(51) Int. Cl.
 *B22F 3/105* (2006.01)
 *B29C 67/00* (2017.01)
 *B33Y 50/00* (2015.01)
(52) U.S. Cl.
 CPC ....... *B22F 2003/1057* (2013.01); *B33Y 50/00* (2014.12); *Y02P 10/295* (2015.11)
(58) Field of Classification Search
 USPC .......................................................... 702/155
 See application file for complete search history.

(56) References Cited

OTHER PUBLICATIONS

Lijun Song et al., "Feedback Control of Melt Pool Temperature During Laser Cladding Process," IEEE Transactions on Control Systems Technology, 19(6):1349-1356 (2011).

* cited by examiner

PROCESS MAPPING OF COOLING RATES AND THERMAL GRADIENTS

CROSS-REFERENCE TO RELATED APPLICATIONS

This application claims the benefit of priority under 35 U.S.C. § 119(e) to provisional U.S. Patent Application No. 61/742,734, filed on Aug. 17, 2012, and is related to International Application No. PCT/US2012/048658, filed on Jul. 27, 2012, the entire contents of each of which are hereby incorporated by reference.

STATEMENT REGARDING FEDERALLY SPONSORED RESEARCH AND DEVELOPMENT

This invention was made with partial government support under grants CMMI-0700538, CMMI-0700509, CMMI-1131579, and CMMI-1131266 awarded by the National Science Foundation, and under a National Defense Science & Engineering Graduate Fellowship. The government has certain rights in the invention.

FIELD OF USE

The present disclosure relates to process mapping for manufacturing processes.

BACKGROUND

Additive manufacturing (AM), also known as direct digital manufacturing, refers to a wide range of processes for the direct fabrication of final parts, functional prototypes, or both using rapid prototyping technology. In AM, parts are fabricated by deposition using a heat source to locally melt material, forming a melt pool. As the heat source is translated across the part being fabricated, a bead consisting of the moving melt pool with solidified material behind it is formed. Material is fed into the melt pool (either directly or via a powder applied to the surface of the part), and the part is built up one melt pool bead at a time. AM is used for Free Form Fabrication ($F^3$), which is the rapid manufacture of a complete part, and for additive manufacturing and repair (AMR), which adds one or more features to an existing component, either as a manufacturing step or for component repair. For instance, AM can be used to build parts from titanium alloys, which has potential applications in the aerospace and medical implant industries.

SUMMARY

The present disclosure describes methods and apparatus relating to process mapping for manufacturing processes, such as additive manufacturing (AM). In an AM process, a part is fabricated by deposition of successive beads of molten material. AM and other similar manufacturing processes are controlled by primary process variables, including, for instance, heat source power (P), translation speed (V) of the heat source, and feed rate of the source material (MFR). The role of identified primary process variables may be mapped in determining defined cooling rates and thermal gradients resulting from thermal deposition of the bead. The resulting process maps may be used to set primary process variables in order to achieve a desired result (e.g., linked to microstructure formation) in a manufacturing process.

The techniques described herein are applicable to the deposition of single beads of material onto an existing large plate, which is a test that is often used to characterize the performance of a manufacturing tool or machine. The techniques can be applied to the control of cooling rates and thermal gradients during the fabrication of complex three-dimensional shapes. The techniques can be applied to processes where no material is added. The techniques can be applied to map any quantity involving temperature derivatives in a thermal field within or around a melt pool, or any quantity involving temperature derivatives in processes that do not include a melt pool. The techniques can be applied to processes using any type of heat source, including AM processes using a laser or electron beam as a heat source.

In one aspect of the present disclosure, a method includes conducting a plurality of tests of a manufacturing process, each test conducted at a different combination of at least a first process variable and a second process variable, each test comprising: locally heating a region of a structure, wherein the local heating results in formation of a thermal field in the structure, and assessing a temperature derivative of the thermal field; and based on results of the plurality of tests, generating a process map of the temperature derivative of the thermal field, with the temperature derivative based on a function of the first process variable and the second process variable.

1. Implementations of the disclosure may include one or more of the following features. Locally heating the region comprises depositing a bead of material onto a surface of the structure, and wherein the thermal field comprises a melt pool. Depositing the bead of material comprises melting a material source with a heat source. Locally heating the region comprises forming a melt pool on a surface of the structure, and wherein the thermal field comprises the melt pool. The manufacturing process comprises an additive manufacturing (AM) process. The first process variable and the second process variable are each selected from the group consisting of a power (P) associated with the manufacturing process, a translation speed (V) associated with the manufacturing process, a material feed rate (MFR) used in the manufacturing process, a ratio of deposited to remelted area ($\gamma$), a structure geometry, and a structure temperature ($T_o$) away from a heat source used to locally heat the region of the structure. The plurality of tests is conducted with process variables other than the first and second process variables held constant. Assessing the temperature derivative of the thermal field comprises evaluating the temperature derivative at a location on a solidification boundary of the thermal field with increased distance from a heat source used to locally heat the region of the structure, relative to other distances of other solidification boundaries from the heat source. The temperature derivative of the thermal field comprises at least one of a thermal gradient and a cooling rate. The thermal gradient is defined as a gradient vector G, with G being in accordance with $$G = |\nabla T| = \left|\frac{\partial T}{\partial x}\vec{i} + \frac{\partial T}{\partial y}\vec{j} + \frac{\partial T}{\partial z}\vec{k}\right| = \sqrt{\left(\frac{\partial T}{\partial x}\right)^2 + \left(\frac{\partial T}{\partial y}\right)^2 + \left(\frac{\partial T}{\partial z}\right)^2}.$$

Assessing the temperature derivative of the thermal field comprises: determining a contour of the thermal field for a temperature; and evaluating a component of the gradient vector at one or more locations along the contour. The cooling rate is defined as a quantity T', with T' being defined in accordance with $$T' = \frac{\partial T}{\partial t}.$$

The method may include accessing information indicative of an operating range of the manufacturing process; wherein conducting the plurality of tests comprises conducting tests spanning the operating range of the manufacturing process. Generating the process map comprises generating a process map based on an interpolation of the temperature derivative. The tests comprise one or more experimental tests. The tests comprise one or more simulations. The method may include conducting at least one additional test; and adjusting the process map based on results of the at least one additional test. The method may include using the process map to select values of the first and second process variables to yield a selected temperature derivative of the thermal field. The method may include generating a plurality of process maps characterizing the manufacturing process for forming the structure, each process map corresponding to at least one of a geometry of the structure and a temperature of the structure. The method may include decomposing a fabrication of a complex structure into a combination of one or more geometries; and controlling the fabrication of the complex structure based on the process maps for forming each of the one or more geometries. A geometry of the complex structure includes at least one of a height of the complex structure and a width of the complex structure. The structure comprises a part that is used in the manufacturing process.

All or part of the foregoing may be implemented as a computer program product including instructions that are stored on one or more non-transitory machine-readable storage media, and that are executable on one or more processing devices. All or part of the foregoing may be implemented as an apparatus, method, or electronic system that may include one or more processing devices and memory to store executable instructions to implement the stated functions.

Particular implementations of the subject matter described in this disclosure may be implemented to realize one or more of the following potential advantages. The generation of process maps may enable the relationships between process variables and final part quality to be understood with minimal experimentation or simulation. The processing knowledge that may be gained from the process mapping techniques described herein can be extended over a wide range of process variables, thus providing a way to compare results from different pieces of equipment, different manufacturing techniques, or both. Furthermore, the techniques described herein can be used as the basis for an evolving database characterizing the deposition of complex shapes.

Details of one or more implementations are set forth in the accompanying drawings and the description below. Other features, objects, and advantages will be apparent from the description, the drawings, and the claims.

DETAILED DESCRIPTION

While various implementations of the present disclosure are discussed below in the context of additive manufacturing (AM), the techniques described in this disclosure are generally applicable to a wide range of thermal processing systems and techniques. Although AM processes are typically used to fabricate metal structures or parts, the techniques described in this disclosure can be used to support the fabrication of structures or parts of any material compatible with AM processing, welding, beam-based surface heat treating, or other similar manufacturing processes. While specific implementations are described, other implementations may exist that include operations and components different than those illustrated and described below.

Figure 1:
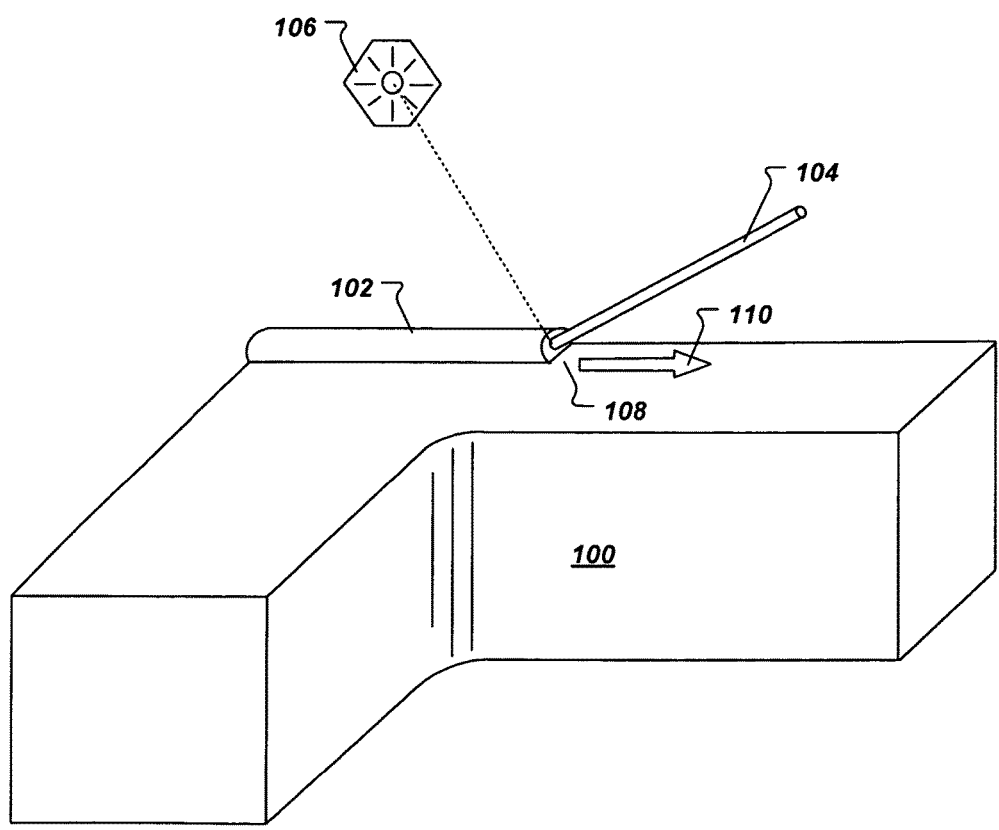
FIG. 1 is a block diagram showing an example of geometry deposition using a beam-based additive manufacturing process.

FIG. 1 is a block diagram showing an example of geometry deposition using a beam-based additive manufacturing (AM) process. In a beam-based AM process, a structure or part 100 is fabricated by deposition of successive beads 102 of molten material. The material is provided from a material source 104, such as a wire feed (as shown), a powder feed, or a powder bed. While the techniques described herein can be used to develop AM or direct digital manufacturing processes that involve the feeding of material in wire or powder form into a melt pool, the techniques may also be applied to other AM processes that do not involve the direct feeding of material into a melt pool, such as powder bed AM processes and analogous welding processes.

A heat source 106, such as an electron beam, a laser beam, or an electric arc, melts the material source 104 to generate the bead 102 while melting some of the top surface 108 of the part 100. The heat source 106 is translated relative to the part 100 (or the part 100 is translated relative to the heat source 106) to cause deposition of the bead 102 in a desired geometry and a desired direction 110 to form the part 100. Other suitable heat sources can be used. For example, different welding processes use a variety of mechanisms for heating, including a metal arc, gas combustion, electrical resistance, friction, and ultrasonics. In another example, extrusion-based polymer additive manufacturing processes deposit preheated material onto the surface of a growing part. In that case, the heat in the added material may be treated as the heat source.

For a single, specified material, the primary process variables that control AM processes are the power (P) of heat source 106, the translation speed (V) of the heat source 106, the material feed rate (MFR, in units of volume per time) of the material source 104, the local geometry being deposited (e.g. a single bead geometry), and the temperature ($T_0$) of the part 100 away from the heat source 106. These process variables also control other similar manufacturing processes, such as welding processes and beam-based surface heat treating processes (which would involve the limiting case of MFR=0). Secondary process variables and conditions can also affect processing, including, for instance, beam focus, wire or powder diameter, deposition environment (e.g., deposition in a vacuum or in an inert gas environment), and other variables.

Figure 2:
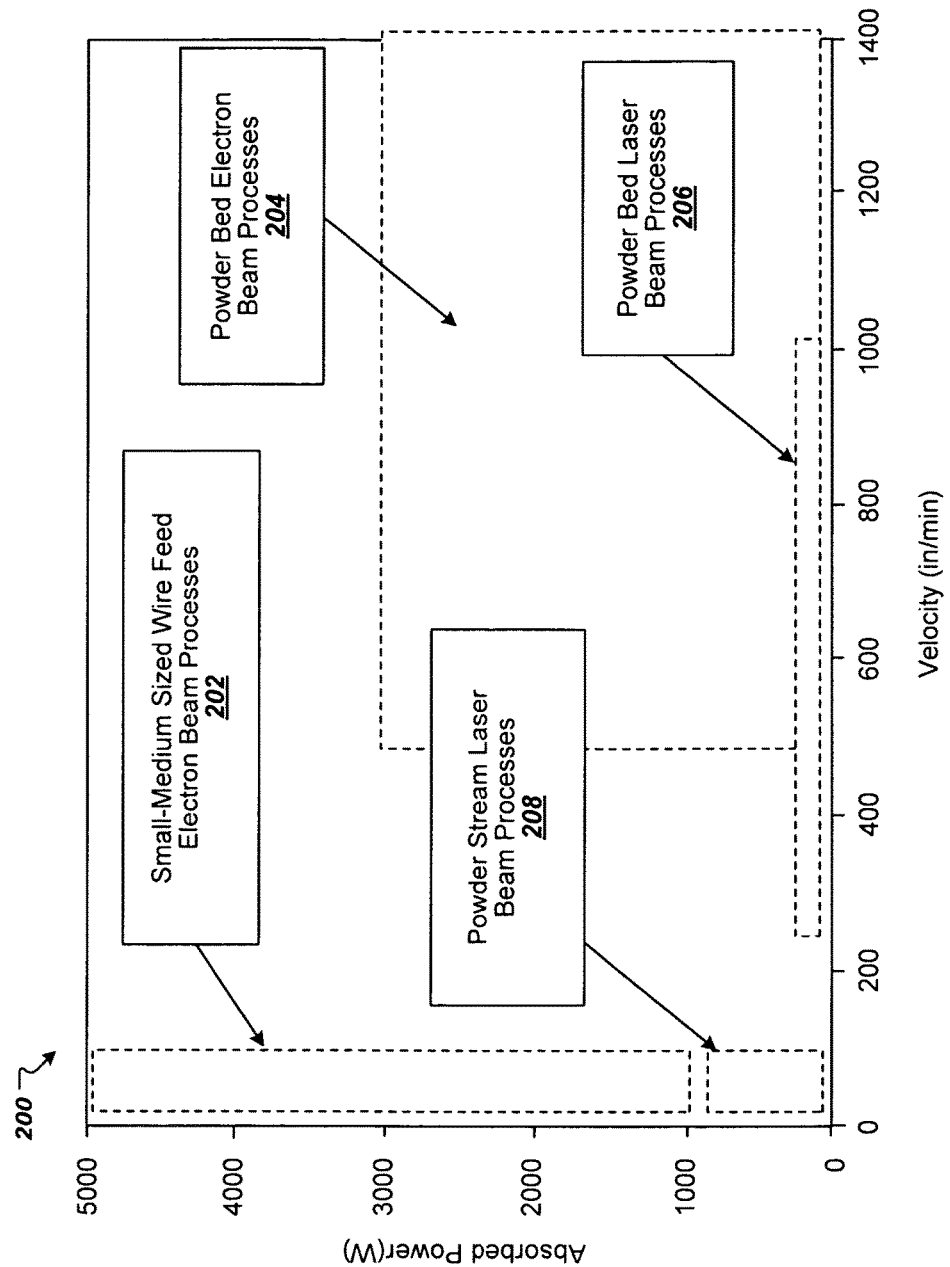
FIG. 2 is a plot of approximate ranges of power and velocity used in examples of additive manufacturing processes for metals.

FIG. 2 is a plot 200 of approximate ranges of power and velocity used in examples of additive manufacturing processes for metals. Many types of manufacturing processes spanning a wide range of process variables fall under the purview of AM processing. For instance, AM processes include small- and medium-scale electron beam wire feed processes 202, electron beam powder bed processes 204, laser power bed processes 206, and laser powder stream processes 208. Large-scale electron beam processes operating at beam powers of, e.g., 20 kW or more (not shown in FIG. 2), may also be considered to be AM processes. The techniques described herein are applicable to the full range of process variables used in these and other AM processes.

Figure 3:
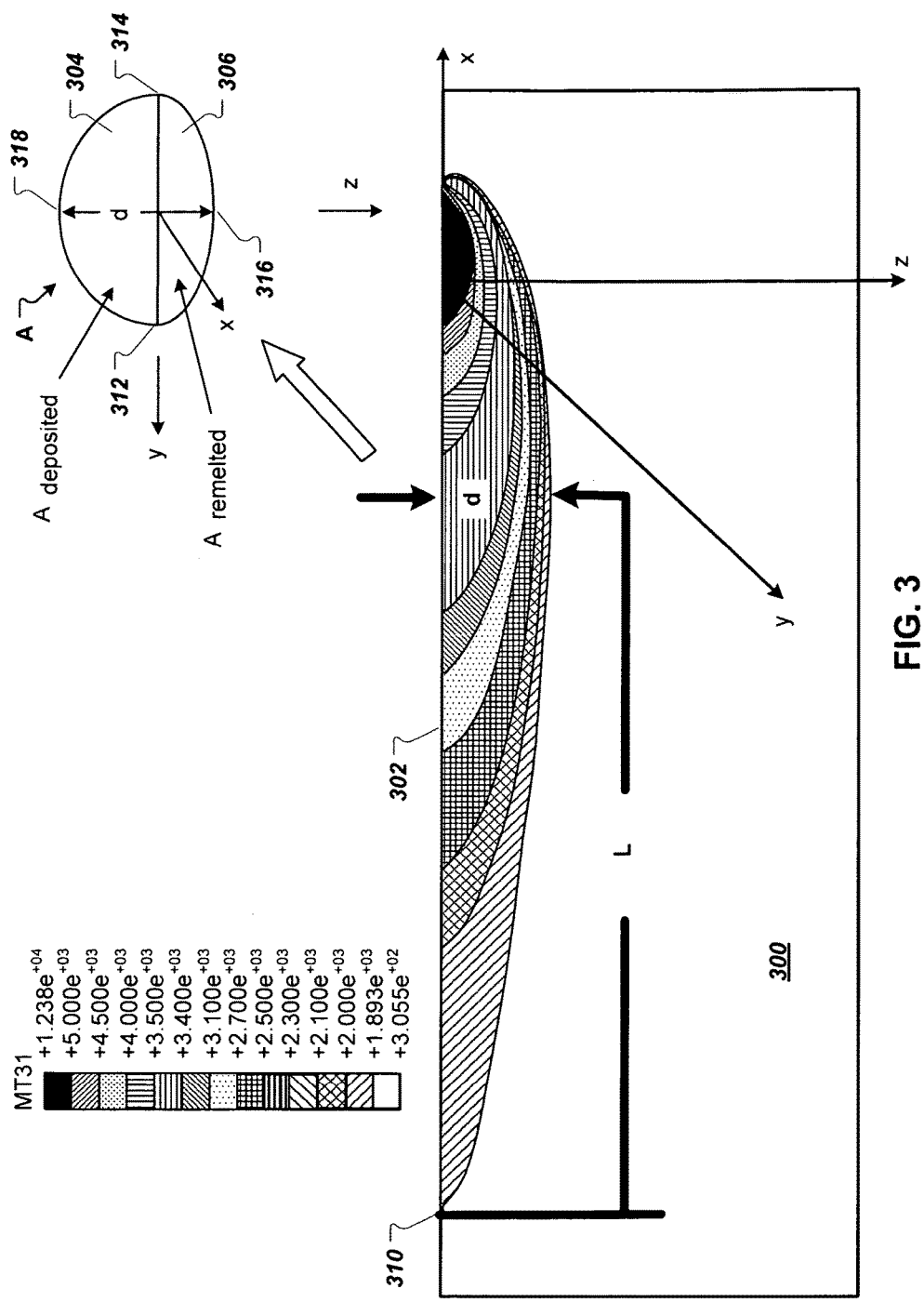
FIG. 3 is a diagram of melt pool dimensions and locations.

In addition to AM processes, the techniques described herein can be applied to a variety of processes, such as welding processes, involving the formation of a melt pool, even if not used to build a shape. FIG. 3 is a diagram of melt pool dimensions and locations. When a bead of material is deposited onto a surface of a part 300 in an AM process, a melt pool 302 is formed including the molten bead 304 of material and any material 306 of the surface that has melted as a result of the bead deposition. A side-view cross-section of the melt pool 302 on the surface of the part 300, derived from a finite element model, depicts melt pool dimensions and locations that may be relevant to process control. FIG. 3 also illustrates thermal contours within the melt pool. In FIG. 3, the melt pool 302 is moving in the positive x direction (i.e., the direction of V).

While FIG. 3 describes a melt pool, a melt pool is not required. Generally, when a local heat treatment is applied to a region of a part (e.g., via a moving heat source), a thermal field is created in the part. In some instances, some of the thermal field is melted; in other instances, the temperatures of the thermal field are raised relative to the temperature of the surrounding material, but melting does not occur. For example, in beam-based surface heat treating processes in which a beam is rapidly moved across a surface to alter near-surface microstructure without melting, the techniques described in this disclosure can be used to map critical cooling rates and thermal gradients. In the following description, reference is made to the dimensions of a melt pool; however, the dimensions of a thermal field may be treated similarly to the dimensions of a melt pool.

In FIG. 3, the maximum melt pool cross-sectional area, A, is the area of the melt pool 302 normal to the x-axis (and thus normal to the direction of travel of the melt pool 302), at the deepest point of the melt pool 302. The melt pool length, L, is the length of the melt pool 302 from the x location of A to a location 310 of the trailing tip of the melt pool 302. The melt pool depth, d, is indicative of the maximum depth of the melt pool 302. In some instances, d is the actual maximum depth of the melt pool 302. In other instances, d is an effective depth of the melt pool 302 as calculated from A using the formula $d=\sqrt{2A/\pi}$. The maximum melt pool cross-sectional area, A, equals the cross-sectional area ($A_{deposited}$) of the deposited bead 304 plus the cross-sectional area ($A_{remelted}$) of the material 306 melted on the surface of the part 300. The melt pool length, L, relates to the shape of the solidification front behind the melt pool 302. In some cases, a dimensionless variable, L/d, is used, which relates to the aspect ratio or shape of the trailing end of the melt pool 302.

The part temperature, $T_0$, can be due to active preheating of the part through external means or can be due to heat build-up from a heat source, e.g., caused by prior deposition of material. Part temperature away from the heat source is easily monitored in real time. Any location may be selected for monitoring $T_0$, provided the location is away from the local thermal field of the heat source and is consistent throughout the tests (simulations or experiments).

In other embodiments, an alternative primary variable, γ, can be used in place of the MFR. The variable γ, which represents the deposited to remelted area ratio ($\gamma=A_{deposited}/A_{remelted}$), directly relates the size of the added bead of material to the size of the material melted in the existing part and thus relates the effect of those sizes on heat transfer into the part. The variables γ and MFR are related. Specifically, MFR=$V*A_{deposited}$, where $A=A_{deposited}+A_{remelted}$. From these relationships, it can be determined that $$MFR = V*A/\left(1+\left(\frac{1}{\gamma}\right)\right).$$

In manufacturing applications, γ is bounded by a value of 0 (for no added material) to infinity (for no remelting of the substrate material). When process mapping is used to determine the role of process variables on melt pool dimensions, to determine how local bead geometry affects melt pool dimensions, or to determine both, the use of γ may be more relevant. For manufacturing control, MFR may be the more relevant variable.

Other process variables, such as an alternative process variable that relates to the local geometry of the melt pool, may also be used for process mapping. For example, the variable $\phi=A_{deposited}/A$ may be used. The variable φ takes on a role similar to γ, except that φ has an operating range from 0 (for no added material) to 1 (for no remelted substrate material). In another example, in powder bed AM processes, material is added in the form of a thin layer of powder spread across the part surface. In that case, the layer thickness, t, may be used as a variable related to MFR.

The role of primary process variables may be mapped in determining temperature derivatives resulting from deposition of a bead as secondary process variables are held constant. In some implementations, secondary process variables may vary and are determined by the primary process variables. In cases where secondary process variables change independently or randomly, their effect on temperature derivatives may be identified by first separating out the role of the primary process variables.

The role of primary process variables may be mapped on temperature derivatives, e.g., any derivative (spatial or temporal) of the temperature field, at a location along the solidification boundary of the melt pool 302. Dimensions (e.g., lengths, widths, or areas) of regions bounded by constant values of a temperature derivative quantity may also be mapped. Examples of temperature derivatives are thermal gradient or cooling rate. Thermal gradient and cooling rate along the solidification boundary may be related to the formation of microstructure at the melting temperature in metals. Specifically, the thermal gradient vector, G, is defined as the quantity $$G = |\nabla T| = \left|\frac{\partial T}{\partial x}\vec{i} + \frac{\partial T}{\partial y}\vec{j} + \frac{\partial T}{\partial z}\vec{k}\right| = \sqrt{\left(\frac{\partial T}{\partial x}\right)^2 + \left(\frac{\partial T}{\partial y}\right)^2 + \left(\frac{\partial T}{\partial z}\right)^2}.$$

The cooling rate, T', is defined as the quantity $$T' = \frac{\partial T}{\partial t}.$$

Temperature derivative quantities can be extracted from process simulations or from experiments (e.g., from thermal imaging of surface temperatures).

Cooling rates and thermal gradients may be evaluated at specific x, y, and z coordinates, or, for example, at a specified temperature and two coordinate locations. As an example, evaluating G and T' at the melting temperature specifies that they be evaluated along the solidification front of the melt pool 302, which is its trailing surface behind (to the left of) the melt pool area, A. To properly define G and T', two coordinate locations, e.g., y and z locations, on the solidification front (or boundary) is also specified. In general, G and T' may vary with y and z locations, and thus, a full understanding of microstructure formation may require evaluation of G and T' at many y and z locations. However, in some cases locations 310 (at the trailing tip of the melt pool), 312, 314, 316, and 318 (at the left, right, top, and bottom extremes of A) may be key locations to consider. Of these locations, location 310 may have the lowest thermal gradient, due to being furthest (e.g., with increased distance) from the heat source relative to other locations on the solidification front, so evaluating G and T' at location 310 can establish lower bounds on G and T' at the melting temperature.

While G and T' may be evaluated at point 310 of FIG. 3, any temperature derivative quantity at any location may be evaluated and mapped. For instance mapping the magnitude of the gradient vector component in the z direction at a temperature below the melting temperature would involve first determining a thermal contour for that temperature, and then picking one or more locations along that thermal contour to evaluate the z component of the gradient vector. In some applications to predicting microstructure, combinations of temperature derivative quantities may be important and can also be mapped. For instance, the morphology of beta grains formed during the solidification of the titanium alloy Ti-6Al-4V can be expressed in terms of G and the quantity $$R = \frac{1}{G}\frac{\partial T}{\partial t}.$$

As another example, dimensions (e.g., lengths, widths, areas) of volumes bounded by specified cooling rates could also be mapped. Higher order spatial or temporal derivatives of temperature could also be mapped. In cases where microstructure is tied to temperature derivative quantities, experimentally determined microstructural measurements (e.g., grain sizes and grain morphologies determined from cross section microscopy) can also be mapped.

Process mapping of the deposition of single beads of material onto an existing large plate is a test that may be used to characterize the performance of an AM machine or other manufacturing tool. The techniques for process mapping of the deposition of single beads of material may be applied to the fabrication of more complex 3-D shapes. Process mapping of the deposition of complex 3-D shapes can be decomposed into combinations of simpler, commonly fabricated geometries, each of which may have one or a series of associated process maps. FIGS. 4-12 are block diagrams showing examples of commonly fabricated geometries or features. These commonly fabricated geometries or features are not exclusive, and process maps may be constructed for any other relevant geometry in a similar manner.

In the geometries shown in FIGS. 4-12, the coordinate origin is taken to be the location where the heat source is positioned, and deposition proceeds in the positive x direction. In the geometries shown in FIGS. 4-9 (referred to as "steady-state geometries"), the geometry is constant in the deposition direction (away from free edges of the geometry). In the geometries shown in FIGS. 10-12 (referred to as "transient geometries"), the geometry changes in the deposition direction.

For the steady-state geometries shown in FIGS. 4-9, if process variables are held constant during deposition, the near-melt-pool thermal field does not change, because the geometry of the feature does not change in the deposition direction. In general, process mapping may be directly applicable to these steady-state geometries.

Figure 10:
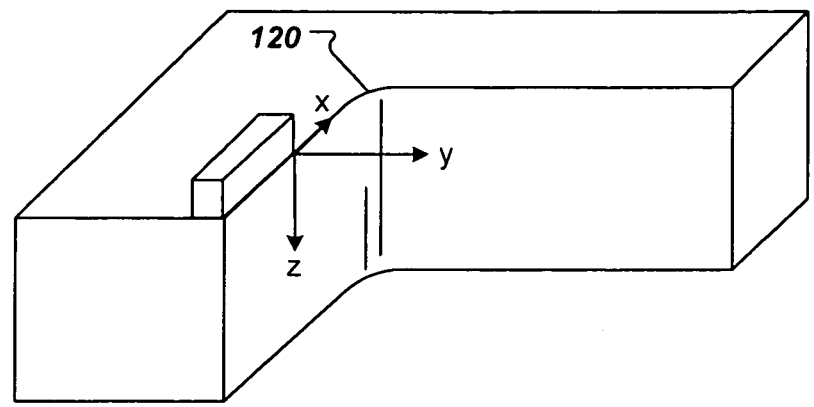
FIG. 10 is a block diagram of an internal radius geometry.
Figure 11:
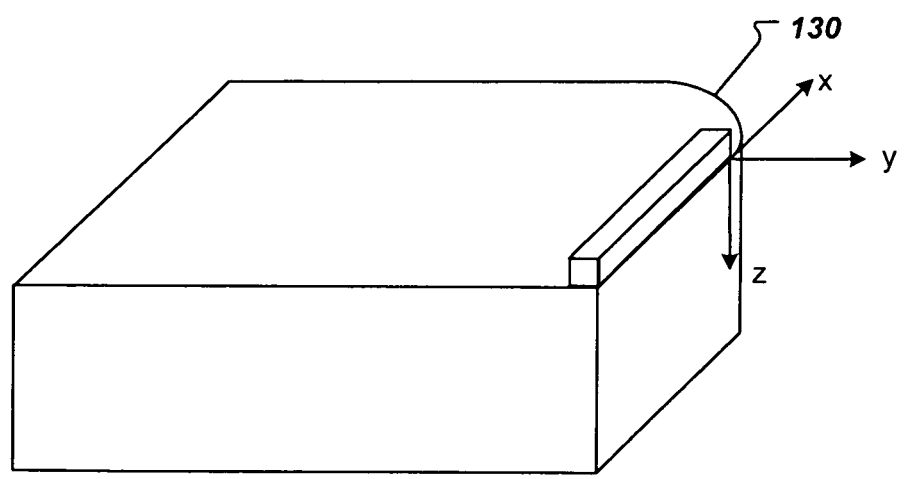
FIG. 11 is a block diagram of an external radius geometry.
Figure 12:
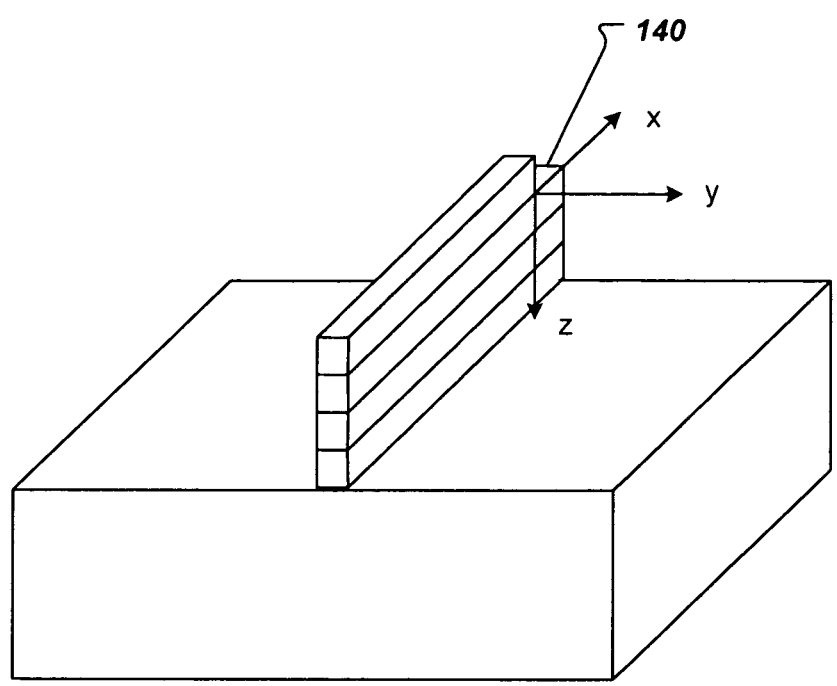
FIG. 12 is a block diagram of an approaching edge geometry for a thin wall.

For the transient geometries shown in FIGS. 10-12, as deposition progresses under constant P and V conditions, the near-melt-pool thermal field is generally changed via its interaction with a radius or free edge. Process mapping can also be applied to map these transient geometries; however, for each combination of process variables, temperature derivative quantities will generally be a function of location of the moving heat source as it travels through the changing geometry.

Figure 4:
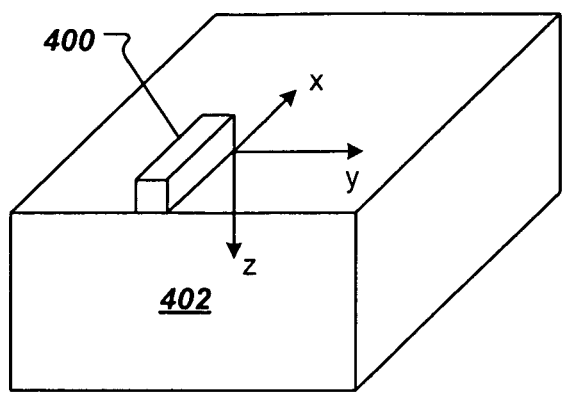
FIG. 4 is a block diagram of a single bead geometry.

FIG. 4 is a block diagram of a single bead geometry. Single bead deposition is often used as a test to characterize or evaluate the performance of an AM machine. In single bead deposition, a single bead 400 of material is deposited onto a flat plate 402. In general, the plate 402 is large enough in the x and y directions that the melt pool geometry in the middle of the plate 402 (and thus probably other characteristics of the near-melt-pool thermal field) are not affected by the free edges of the plate 402. The plate thickness (in the z direction) may be large enough that the bottom surface does not affect the near-melt-pool thermal field. Alternatively, the plate thickness may be a thickness selected by a user and held constant across all tests.

Figure 5:
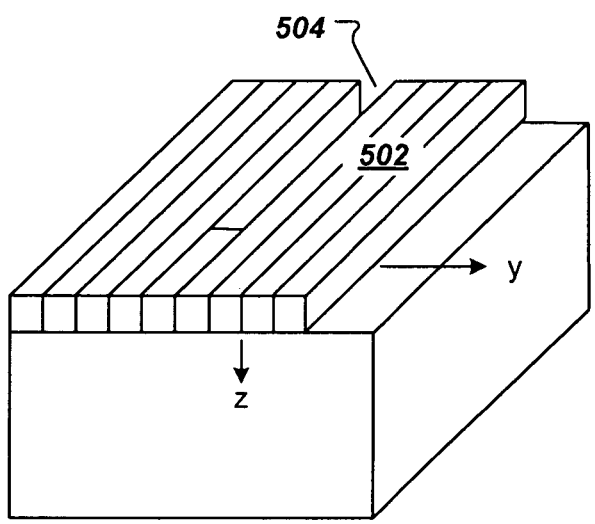
FIG. 5 is a block diagram of a fill geometry.

FIG. 5 is a block diagram of a fill geometry. For this geometry, many beads 502 are assumed to exist on either side of a channel 504 that is being filled, so the effect of the number of beads 502 on either side is not generally mapped out. This geometry is very similar to the case of adding no material at all (where $\gamma=0$), with a beam simply translated across a large plate. However, when no material is added, conduction into material ahead of the moving beam is allowed. In the fill case, the material ahead of the moving beam is not present.

Figure 6:
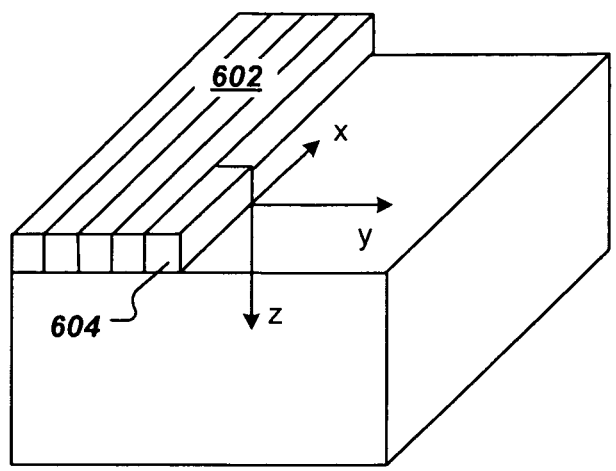
FIG. 6 is a block diagram of a sequential bead geometry.

FIG. 6 is a block diagram of a sequential bead geometry. The sequential bead geometry may be used to fill an internal area, ultimately ending with the fill geometry of FIG. 5. In this case it is assumed that many beads 602 exist to the left of a bead 604 being deposited.

Figure 7:
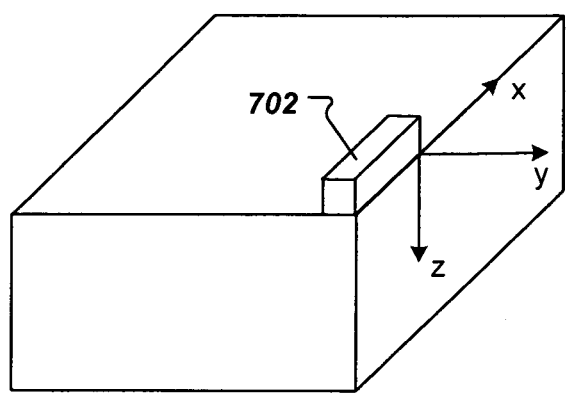
FIG. 7 is a block diagram of a free edge geometry.

FIG. 7 is a block diagram of a free edge geometry. Free edge geometry uses a bead 702 to define an outer perimeter of a layer. Multiple geometries may be considered as the beads move in away from the edge. For instance, the number of beads that are sufficient to reach steady state and to yield the same results as the sequential bead geometry of FIG. 6 may be determined.

Figure 8:
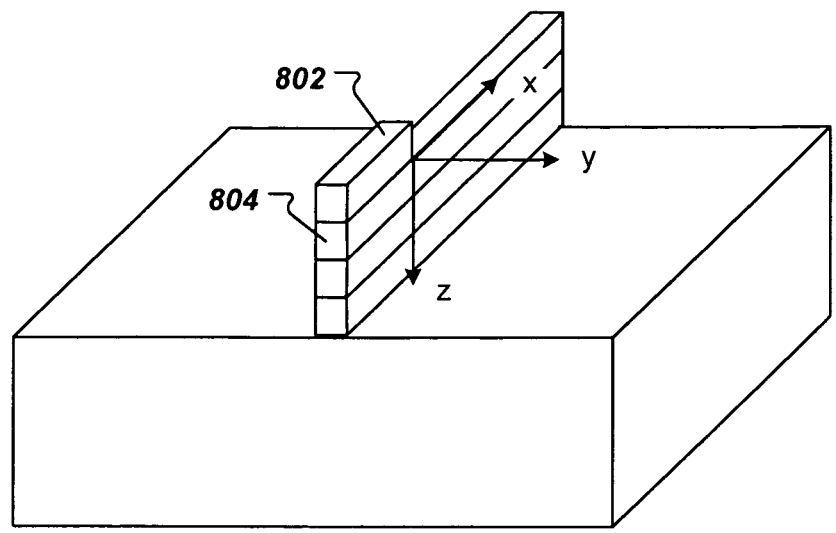
FIG. 8 is a block diagram of a single pass thin wall geometry.

FIG. 8 is a block diagram of a single pass thin wall geometry. A single pass thin wall consists of a single bead geometry 802 deposited successively on top of another single bead geometry 804. As the thin wall is built, the geometry approaches a steady-state "tall wall" limit that is independent of wall height. A single pass thin-walled cylinder may also be considered a single pass thin wall, provided the radius of curvature of the cylinder is not too small.

Figure 9:
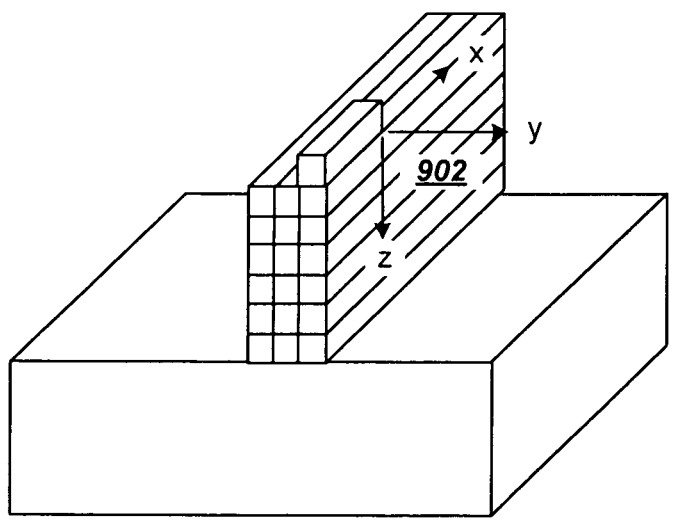
FIG. 9 is a block diagram of a multi-pass thin wall geometry.

FIG. 9 is a block diagram of a multi-pass thin wall geometry. In some implementations, free edges of a wall 902 can be deposited first. In an example, once the edges are deposited, the wall 902 is filled. In some implementations, the wall is constructed by starting at one face and progressing across the thickness of the wall 902. Other implementations are possible. Multiple wall thicknesses may be mapped prior to reaching a "thick wall" limit. For each thickness, there are multiple geometries to consider, including free edge, sequential bead, and fill type configurations. In addition, the height dependence of the wall 902 may be mapped. As with the single pass thin wall, the multi-pass thin wall may also be applied to the deposition of a multi-pass thin-walled cylinder, provided the radius of curvature is not too small.

FIG. 10 is a block diagram of an internal radius geometry. FIG. 11 is a block diagram of an external radius geometry. For these geometries, there are various radii, e.g., internal radius 120 of FIG. 10 and external radius 130 of FIG. 11, to be mapped. In some cases, the ratio of radius to melt pool depth may govern the melt pool behavior. In addition, various turn angles can be mapped; a 90° turn is a common example of a turn angle. The radius geometry may be executed in combination with various geometries, such as the steady-state geometries described above.

FIG. 12 is a block diagram of an approaching edge geometry for a thin wall. Approaching a free edge 140 or leaving a free edge may cause different results and process maps may be developed for both cases.

Figure 13:
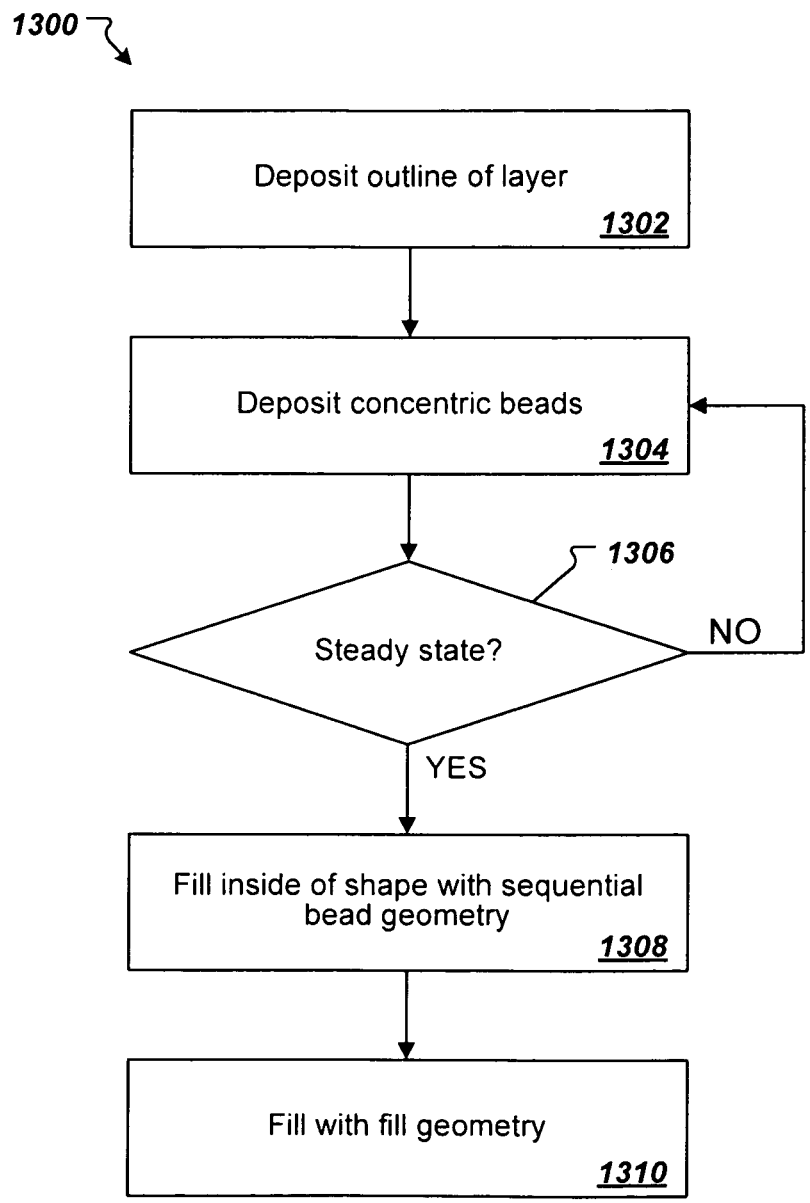
FIG. 13 is a flowchart of an example of a process for depositing a layer of a three-dimensional feature.

FIG. 13 is a flowchart of an example of a process 1300 for depositing a layer of a three-dimensional feature. One or more of the steady-state geometries may be combined to result in the deposition of a single layer of an arbitrary planar shape. The process 300 assumes that the shape is such that radii in the deposition direction are large and that the geometry is not a thin wall, such that the transient geometries described above do not apply.

An outline of the layer is deposited (1302) via the free edge geometry. Successive concentric beads are deposited (1304), still as part of the free edge geometry, moving inwards from the free edge until a steady-state has been achieved (1306). When steady-state is reached, the sequential bead geometry is applied and the inside of the shape is filled in (1308) by a concentric fill path, a raster pattern, or another path. The filling-in operation ends with the fill geometry (1310).

Under this deposition procedure, the edges of the resulting part are smooth because the outline of the part is the first feature to be deposited. In addition, no free edges are approached or left by newly deposited beads, thus allowing these transient geometries to be avoided. In certain cases, such as for a thin wall geometry, depositing the outline of the layer may be impractical or impossible, rendering unavoidable the transient problem of approaching or leaving a free edge.

Figure 14:
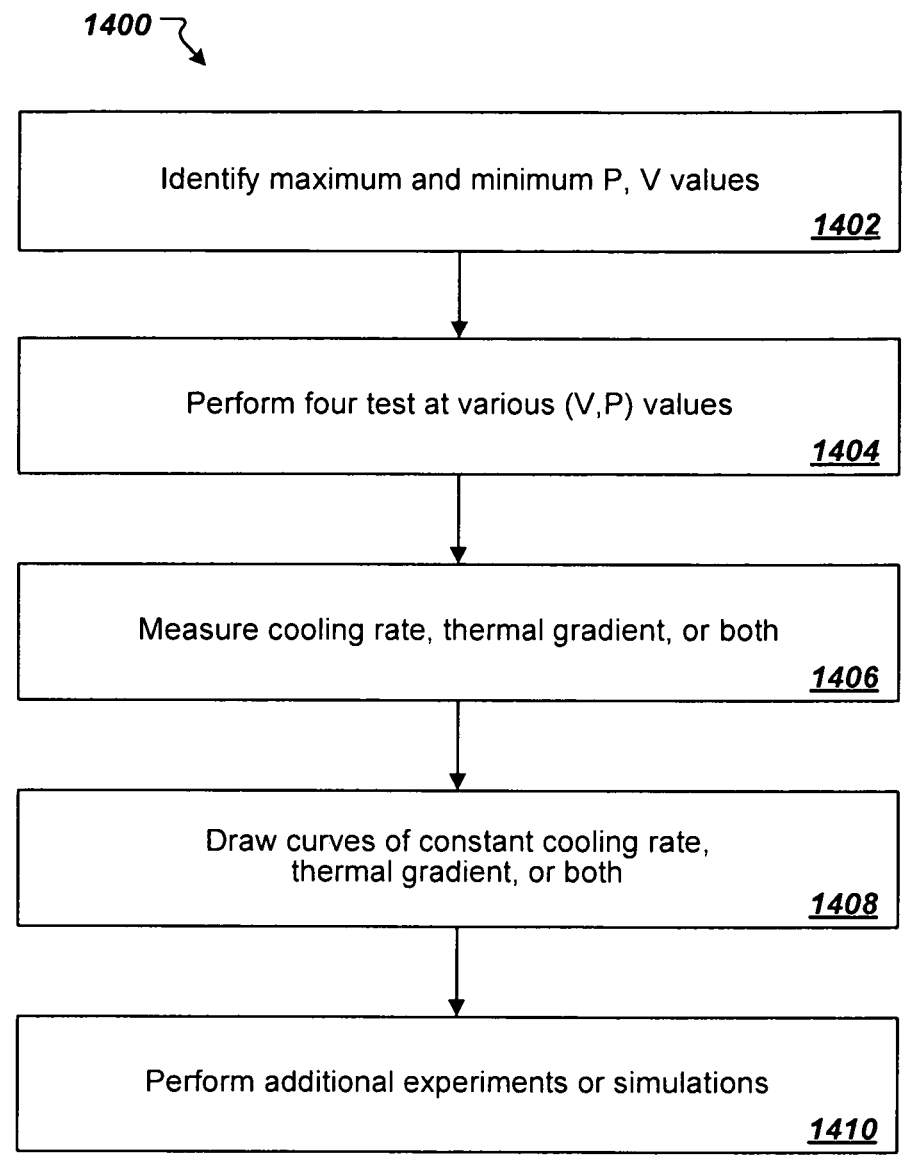
FIG. 14 is a flowchart of an example of a process for generating a power-velocity (P-V) process map for cooling rates and thermal gradients.

FIG. 14 is a flowchart of an example of a process 1400 for generating a power-velocity (P-V) process map for cooling rates and thermal gradients. The process 1400 will be described in the context of AM processes. In AM processing, the value of $\gamma$ is typically held constant, so process maps for a single value of $\gamma$ may be most relevant. Thus, details are given for P-V process mapping for a single value of $\gamma$ using a small number of initial experiments and/or simulations. Process maps for a fixed value of MFR or $\phi$ or other parameter related to MFR may also be developed using similar procedures. Temperature derivatives can also be mapped for multiple values of $\gamma$ (e.g., for selected values of $\gamma$ and/or for the entire range of $\gamma$) using similar techniques.

Other process variables (related to part geometry and far-field temperature $T_0$) are also assumed constant. Thus, the P-V process map will be developed for a single commonly fabricated geometry, or, if the commonly fabricated geometry has a variable associated with it (such as wall height or distance from a free edge), the P-V process map may be determined for a single value of that variable.

In some implementations, the mapping process 1400 may be used to map steady state values of cooling rates and thermal gradients. In some implementations, the mapping process 1400 may be used to track transient responses of these quantities (e.g., how the cooling rate changes as deposition is initiated near a plate edge and progresses toward the plate center). The temperature derivative quantity may be specified as being at a single x, y, and z location, or, for example, at a single temperature and 2 coordinate locations. After developing a P-V process map for single values of $\gamma$, part geometry, $T_0$, and location of the temperature derivative quantity, additional process maps can be developed for different values of these variables.

To generate a P-V process map for a particular temperature derivative quantity evaluated at a single x, y, and z location for a single value of $\gamma$, part geometry, and $T_0$, minimum and maximum P and V values of interest (e.g., a range of P and V relevant to a particular type or types of AM process) are identified (1402) to define the P and V operating ranges for the process map. Identifying the P and V operating ranges may include accessing information indicative of the operating ranges of P and V. Within these P and V ranges, an initial, approximate plot of curves of constant temperature derivative can be generated based on a small number of experimental or simulated tests. The tests may include locally heating a region of a structure, and the local heating results in a formation of a thermal field in the structure. Specifically, four tests can be performed (1404) via experimentation and/or simulation at the following values of (V, P):

1. $(V_{max}, P_{max})$
2. $(V^*, P_{min})$, where $V^*$ is the value of V at $P_{min}$ on a straight line drawn between $(V_{max}, P_{max})$ and $(0,0)$
3. $(V_{min}, P_{max})$
4. $(V_{min}, P_{min})$ In some implementations, initial Test 2 may be performed at $(V_{max}, P_{min})$. However, in some instances, conducting Test 2 at $(V^*, P_{min})$ may produce more precise results than conducting Test 2 at $(V_{max}, P_{min})$. A thermal field will exist for a value of V=0 and a non-zero value of P. Thus, all curves of thermal field derivatives will intersect the P axis above P=0, and process map results of interest should be above the straight line between ($V_{max}$, $P_{max}$) and (0,0).

For these initial tests, γ can be any single value between 0 (no added material) and infinity (no remelted material), and the resulting process map will be for that value of γ. However, because the melt pool areas, A, are not known for each case (assuming no prior experiments have occurred), a nonzero value of γ may not be able to be accurately specified before each test is performed. To address this issue, the first four tests may be performed with γ=0 (no added material). Subsequent tests (see below) can be performed with γ=0 to create an increasingly accurate P-V process map for γ=0. Alternatively, values of A extracted from the first four tests with γ=0 can be used to approximate MFR values associated with a desired, nonzero value of γ in subsequent tests (ultimately creating an accurate P-V process map for a single nonzero value of γ).

For each test, the temperature derivative quantity is measured or assessed (1406), along with A and $A_{deposited}$ (or $A_{remelted}$) to confirm the value of γ. Assessing the temperature derivative can include determining a contour of the thermal field for a temperature, and evaluating a component of the gradient vector at one or more locations along the contour. Once the temperature derivative quantity is obtained from each of the four tests, it can be linearly interpolated between the data obtained from the four tests to generate a first P-V process map of curves of constant temperature derivative (1408).

In particular, for the mapping of cooling rates and thermal gradients, G and T' can be linearly interpolated in terms of V at $P_{min}$ and $P_{max}$. Straight lines of constant T' are drawn from $P_{min}$ to $P_{max}$ based on the linear interpolation. Values of G are then linearly interpolated along the lines of constant T', and straight lines of constant G are drawn. In some cases, these linear interpretations are reasonably accurate. In other cases, (e.g., for certain materials and/or certain process variable ranges), stronger nonlinear behavior in P, V, or both may make these linear interpolations less accurate. In an example, more than four combinations of P and V may be initially tested, with other (e.g. higher order) interpolations made between the points.

Independent of the number of initial data points used and the type of initial interpolations used between them, the constant T' and constant G curves may be defined more precisely through additional experiments and/or simulations (1410), e.g., at midpoint locations between points on the process map representative of existing tests. For instance, a test may be performed at ($V_{min}$, ($P_{max}$+$P_{min}$)/2). Curves may be generated between test data points using, e.g., piecewise linear fitting, $2^{nd}$ order curve fitting, or any other appropriate curve fitting model.

The accuracy of the first process map, the second process map, or both can be increased by performing additional experiments, simulations, or both. If desired, additional process maps may also be generated at different γ values, different geometries or values of the geometric variable for one geometry, and different values of $T_0$. Over time, data can be added to a process map such that the process map more accurately characterizes a particular piece of equipment. In some implementations, the additional experiments and/or simulations may involve changing secondary process variables to quantify their role in changing temperature derivative quantities across the range of primary process variables.

Similar mapping techniques can also be applied to a generalized thermal field, such as a region of a surface (or subsurface) that is heated (that does not have to have a maximum temperature greater than or equal to the melting temperature). Even in the case of the existence of a melt pool, it may be important to quantify temperature derivatives at temperatures above or below the melting temperature (within or outside of the melt pool boundary, respectively). Similar techniques can also be used to map the dimensions of regions bounded by constant values of defined temperature derivatives.

In practice, process mapping may be simplified. For instance, the effect of $T_0$ may only be a concern in certain cases, such as continuous deposition (e.g., no pausing between bead deposition) resulting in heat build-up, or deposition of one bead at a time followed by a pause to allow the part to cool to ambient temperature. If the effect of $T_0$ is only of concern in these cases, process maps can be generated only for these cases. As another example, when a part is actively preheated to a particular $T_0$ value prior to deposition, only a few values of $T_0$ may be of interest. Process mapping for multiple values of γ can be similarly simplified by first constructing maps for the extreme values of γ=0 (no added material) and γ approaching infinity (no remelted material) to determine the importance of γ on the temperature derivatives.

Figure 15:
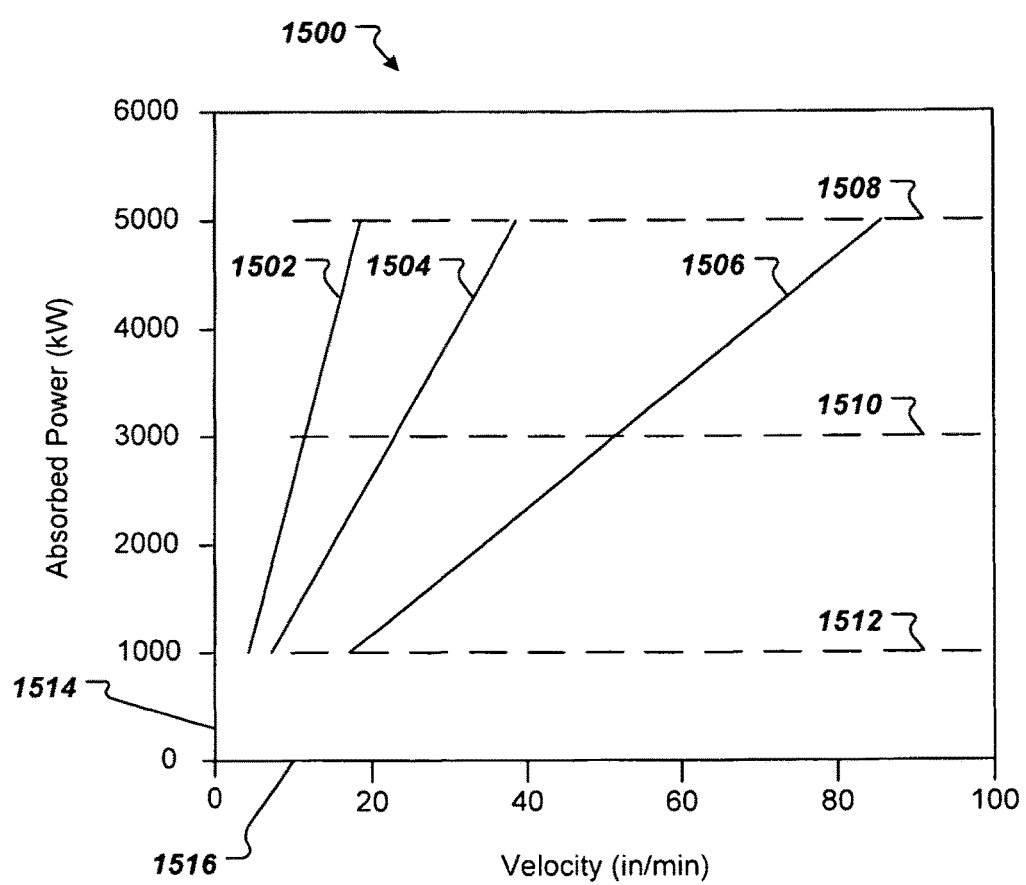
FIG. 15 is an example of a P-V process map showing curves of constant cooling rate (T') and constant thermal gradient (G) for a single bead geometry.

FIG. 15 is an example of a P-V process map 1500 showing curves 1502, 1504, 1506 of constant cooling rate (T') and curves 1508, 1510, 1512 of constant thermal gradient (G) for a single bead geometry. Curve 1502 represents T'=297 K/s. Curve 1504 represents T'=544 K/s. Curve 1506 represents T'=1090 K/s. Curve 1508 represents G=7.98$e^5$ K/m. Curve 1510 represents G=13.3$e^5$ K/m. Curve 1512 represents G=39.9$e^5$ K/m.

The P-V process map 1500 shows cooling rate and thermal gradient at a trailing tip of a melt pool (e.g., location 310 in FIG. 3) and is based on numerical modeling of a wire feed electron beam AM process over multiple simulations. The map 1500 is for the deposition of a single bead of titanium alloy Ti-6Al-4V (referred to herein as Ti64) with a single value of γ and $T_0$. The minimum and maximum P values are approximately 1 kW and 5 kW, respectively, as shown by axis 1514, and the minimum and maximum V values are approximately 5 in/min and 100 in/min, respectively, as shown by axis 1516.

For Ti64 in the range of P and V values shown in the example of FIG. 15, curves 1502, 1504, 1506 of constant T' are essentially linear, and interpolations between curves 1502, 1504, 1506 of constant T' in terms of V are also nearly linear, thus suggesting that the use of linear interpolation for T' is relatively accurate. Curves 1508, 1510, 1512 of constant G are also essentially linear (they are essentially horizontal lines), so that a linear fit yields a reasonable first estimate for G values also.

Process maps may be used to set primary process variables in order to achieve a desired result in a manufacturing process. For instance, the process maps may be used as a guide to selecting appropriate values of primary process variables to yield a desired, selected, or pre-determined thermal gradient or cooling rate at a specified temperature and location in order to control microstructure formation. The process maps may also be used as a guide to changing primary process variables in order to maintain a desired, selected, or pre-determined cooling rate or thermal gradient.

Figure 16:
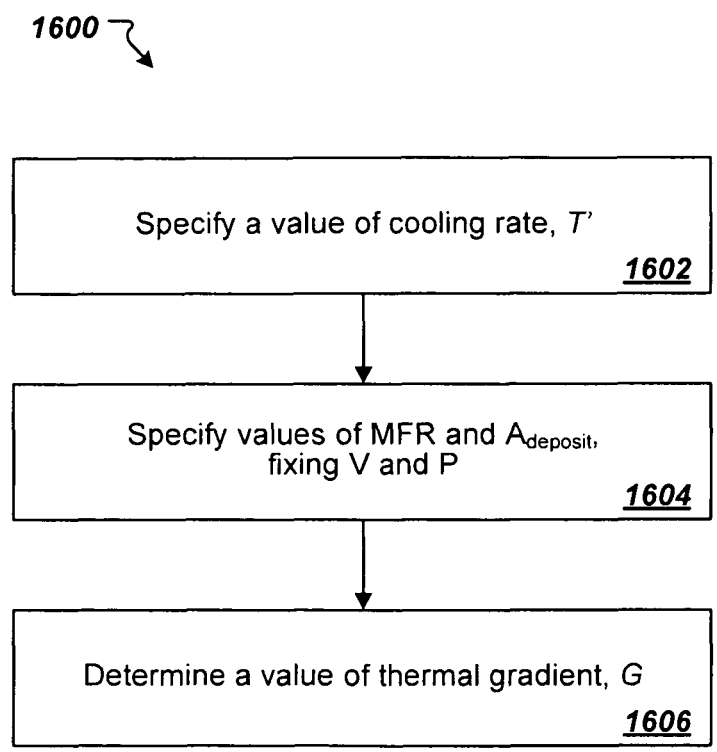
FIG. 16 is a flowchart of an example of a process for using a P-V process map for T' and G.

FIG. 16 is a flowchart of an example of a process 1600 for using a P-V process map for T' and G (e.g., process map 1500 of FIG. 15). Once the P-V process map in terms of T' and G is constructed, the P and V values yielding a desired T', $A_{deposit}$, and MFR (in units of volume/time) can be determined. In some implementations, the P and V values are determined as follows. First, a desired value of T' is specified (1602), fixing the constant T' curve to be used (or a T'curve between the plotted ones). A desired value of MFR is then specified along with a value of $A_{deposit}$ (1604). Because MFR=V*$A_{deposit}$, this fixes V, which in turn fixes P along the constant T' curve. The value of G is then determined from the fixed V and P values (1606). The data in a process map may be used in other ways to determine P and V.

A P-V process map in terms of T' and G can also be used as a guide to maintaining T' or Gas P, V, and MFR are changed. To maintain T' while changing MFR, both P and V are increased or decreased while staying on the relevant constant T' curve. At the same time, MFR is increased or decreased proportionally with V to maintain the γ value of the process map. In moving along the constant T' curve while MFR is adjusted, the value of G is changed. Alternatively, the MFR can be increased or decreased proportionally with V to stay on the relevant constant G curve, causing the value of T' to be changed as G is maintained. Paths on the P-V process map where T' and G are both maintained typically do not exist.

Because it is the simplest commonly fabricated geometry, the single bead geometry and its P-V process map can be used as the basis for comparison for P-V maps of all commonly fabricated geometries. Construction of P-V process maps for commonly fabricated geometries allows temperature derivatives to be maintained across all geometries. Once P-V maps are developed for commonly fabricated geometries, general, complex 3-D part geometries can be fabricated by decomposing the complex geometries into combinations of common, mapped features.

An example of a geometry commonly fabricated by AM is a single pass thin wall (e.g., the single pass thin wall geometry shown in FIG. 8), which is a wall having the width of a single deposited bead, built by depositing one bead on top of another. A series of process maps for T' and G for a point in the middle of the wall (e.g., a point away from the free edges) can be constructed for different heights of the thin wall. Increments in wall height (the geometric variable) can be expressed, e.g., in terms of numbers of beads added to the wall.

A single pass thin wall having a height of only one bead is equivalent to a single bead geometry (e.g., the single bead geometry shown in FIG. 4). When a second bead is deposited on top of the first bead, the wall is hotter (i.e., $T_0$ has been increased), and the change in geometry causes the path of heat conduction into the substrate to be more restricted as compared to the single bead case. These changes may cause changes in the location and shape of the constant T' and constant G curves compared to those for the single bead case. For each wall height (the geometric variable) and $T_0$ of interest, a complete P-V process map can be generated.

In some cases, shortcuts may be used that speed up P-V process mapping by increasing intuition about a system and/or by decreasing the amount of testing or simulation used in the creation of a process map. For example, T' and G may have a limiting upper bound and lower bounds across geometries (for other process variables fixed). Of the geometries described above, a fill geometry (e.g., the fill geometry shown in FIG. 5) has the least restricted path for conduction into the substrate. This bound can be approximated as the case of no added material, so this bound is relatively straightforward to map experimentally by causing a heat source to travel across a large plate. The single pass thin wall geometry with a tall wall has the most restricted path for conduction into the substrate. Thus, the single pass tall wall geometry generally represents another bound in thermal behavior and may yield other bounding values of T' and G. This geometry can be investigated experimentally by depositing onto the top of a thin plate turned on its edge.

In another potential shortcut, generating constant T' and G curves on a P-V process map for the building of a thin wall may cover a wide range of practical P-V behaviors. The first layer of the thin wall is simply the single bead geometry, which is similar to the upper bound fill geometry. The thin tall wall limit yields a lower bound on thermal conditions, as discussed above. Constant T' and G curves for subsequent layers of the thin wall should be between these two extreme cases.

Through the control of cooling rates and thermal gradients, microstructure in metals deposited via AM processes can be controlled. In some implementations, experiments can be performed, followed by cross section microscopy, to qualitatively and quantitatively evaluate microstructural features. Microstructure sizes (e.g., grain size) are typically correlated with cooling rates at certain critical temperatures during cooling in the solid phase. Other microstructural features (such as morphology in the form of either equiaxed or columnar grain structures) can be governed by combinations of thermal gradients and cooling rates. Because of this, observed microstructural features can also be mapped in P-V process space, identifying, for instance, paths of constant grain size (which would be expected to follow curves of constant cooling rate). As an example for the case of equiaxed versus columnar grain morphologies, contours of constant percentages of equiaxed grains could be mapped.

Microstructure can also be indirectly controlled through the control of melt pool geometry (or more generally the indirect control of microstructural features formed at various temperatures through the control of dimensions of the thermal field). International Application No. PCT/US2012/048658 describes the mapping of melt pool dimensions such as A and L. By mapping both melt pool dimensions and T' and G in a process map, the mapping between these quantities can be determined. In some cases, it is possible for the relationships between melt pool geometry and microstructure to be simple. As an example, for single bead deposits for wire feed electron beam AM processes, curves of constant melt pool cross sectional area A are very similar to curves of constant cooling rate at the trailing tip of the melt pool.

Figure 17:
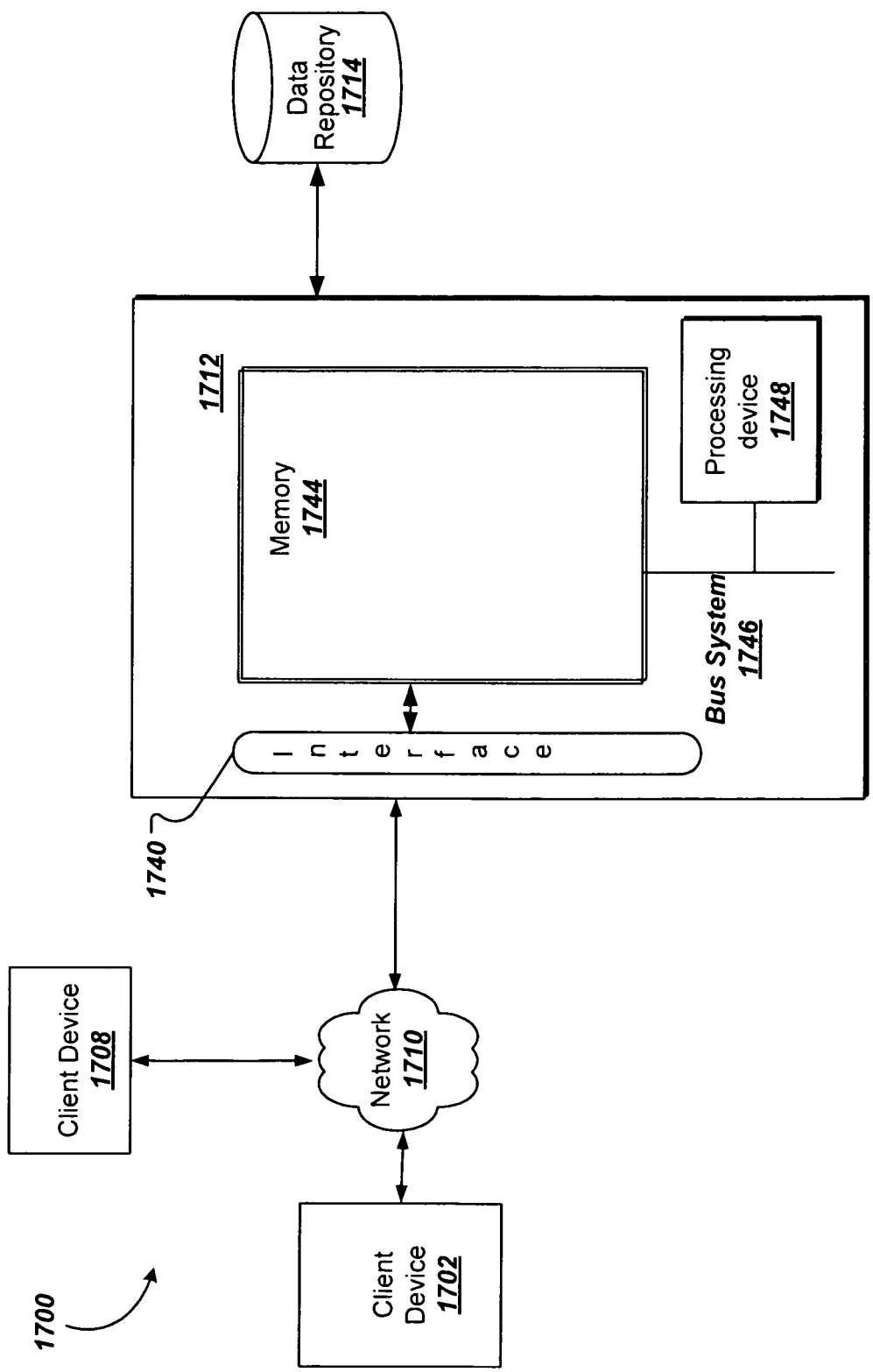
FIG. 17 is a block diagram of an example of a processing system environment.

FIG. 17 is a block diagram of an example of a processing system environment 1700 for generating a process map. In FIG. 17, client devices 1702, 1708 can be any sort of computing devices capable of taking input from a user and communicating over network 1710 with server 1712 and/or with other client devices. For example, client devices 1702, 1708 can be mobile devices, desktop computers, laptops, cell phones, personal digital assistants ("PDAs"), servers, embedded computing systems, and so forth.

Server 1712 can be any of a variety of computing devices capable of receiving data, such as a server, a distributed computing system, a desktop computer, a laptop, a cell phone, a rack-mounted server, and so forth. Server 1712 may be a single server or a group of servers that are at a same location or at different locations. Server 1712 can be configured to execute the techniques and operations described herein to generate a process map. In an example, server 1712 is configured to transmit, over network 1710, information indicative of the generated process map to one or more of client devices 1702, 1708.

The illustrated server 1712 can receive data from client devices 1702, 1708 via input/output ("I/O") interface 1740. I/O interface 1740 can be any type of interface capable of receiving data over a network, such as an Ethernet interface, a wireless networking interface, a fiber-optic networking interface, a modem, and so forth. Server 1712 also includes a processing device 1748 and memory 1744. A bus system 1746, including, for example, a data bus and a motherboard, can be used to establish and to control data communication between the components of server 1712.

The illustrated processing device 1748 may include one or more microprocessors. Generally, processing device 1748 may include any appropriate processor and/or logic device that is capable of receiving and storing data, and of communicating over a network (not shown). Memory 1744 can include a hard drive and a random access memory storage device, such as a dynamic random access memory, or other types of non-transitory machine-readable storage devices. Memory 1744 stores computer programs (not shown) that are executable by processing device 1748 to perform the techniques described herein.

The techniques described herein can be implemented via computational platforms. Various implementations of the techniques described herein can be realized in digital electronic circuitry, integrated circuitry, specially designed ASICs (application specific integrated circuits), computer hardware, firmware, software, or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) include machine instructions for a programmable processor, and can be implemented in a high-level procedural and/or object-oriented programming language, and/or in assembly/machine language. As used herein, the terms "machine-readable medium" and "computer-readable medium" refers to any computer program product, apparatus, and/or device (e.g., magnetic discs, optical disks, memory, Programmable Logic Devices (PLDs)) used to provide machine instructions and/or data to a programmable processor, including a machine-readable medium that receives machine instructions.

Embodiments can be implemented in digital electronic circuitry, or in computer hardware, firmware, software, or in combinations thereof. An apparatus can be implemented in a computer program product tangibly embodied or stored in a machine-readable storage device for execution by a programmable processor; and method actions can be performed by a programmable processor executing a program of instructions to perform functions by operating on input data and generating output. The embodiments described herein, and other embodiments of the invention, can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Computer readable media for embodying computer program instructions and data include all forms of non-volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in special purpose logic circuitry. Any of the foregoing can be supplemented by, or incorporated in, ASICs (application-specific integrated circuits).

Other embodiments are within the scope and spirit of the description claims. Additionally, due to the nature of software, functions described above can be implemented using software, hardware, firmware, hardwiring, or combinations of any of these. Features implementing functions may also be physically located at various positions, including being distributed such that portions of functions are implemented at different physical locations. The use of the term "a" herein and throughout the application is not used in a limiting manner and therefore is not meant to exclude a multiple meaning or a "one or more" meaning for the term "a." Additionally, to the extent priority is claimed to a provisional patent application, it should be understood that the provisional patent application is not limiting but includes examples of how the techniques described herein may be implemented.

A number of exemplary embodiments of the invention have been described. Nevertheless, it will be understood by one of ordinary skill in the art that various modifications may be made without departing from the spirit and scope of the invention.

What is claimed is:

1. A method of controlling microstructural features in additive manufacturing, the method comprising:
    conducting a plurality of tests of an additive manufacturing process, each test conducted at a different combination of at least a first process variable and a second process variable for a structure having a predetermined structure geometry, each test comprising:
        locally heating a region of the structure, wherein the local heating results in formation of a thermal field in the structure having the predetermined structure geometry; and
        assessing a temperature derivative of the thermal field;
    based on results of the plurality of tests, generating a process map of the temperature derivative of the thermal field for the structure having the predetermined structure geometry, with the temperature derivative based on a function of the first process variable, the second process variable, and the predetermined structure geometry; and
    controlling, for the additive manufacturing process, a microstructure formation of a region of the structure having the predetermined structure geometry, the controlling being in accordance with the first and second process variables, to generate a thermal gradient in the structure according to the process map.

2. The method of claim 1, wherein locally heating the region comprises depositing a bead of material onto a surface of the structure, and wherein the thermal field comprises a melt pool.

3. The method of claim 2, wherein depositing the bead of material comprises melting a material source with a heat source.

4. The method of claim 1, wherein locally heating the region comprises forming a melt pool on a surface of the structure, and wherein the thermal field comprises the melt pool.

5. The method of claim 1, wherein the manufacturing process comprises an additive manufacturing (AM) process.

6. The method of claim 1, wherein the first process variable and the second process variable are each selected from the group consisting of a power (P) associated with the manufacturing process, a translation speed (V) associated with the manufacturing process, a material feed rate (MFR) used in the manufacturing process, a ratio of deposited to remelted area ($\gamma$), a structure geometry, and a structure temperature ($T_0$) away from a heat source used to locally heat the region of the structure.

7. The method of claim 1, wherein the plurality of tests is conducted with one or more process variables held constant.

8. The method of claim 1, wherein assessing the temperature derivative of the thermal field comprises evaluating the temperature derivative at a location on a solidification boundary of the thermal field with increased distance from a heat source used to locally heat the region of the structure, relative to other distances of other solidification boundaries from the heat source.

9. The method of claim 1, wherein the temperature derivative of the thermal field comprises at least one of a thermal gradient and a cooling rate.

10. The method of claim 9, wherein the thermal gradient is defined as a gradient vector G, with G being in accordance with $$G = |\nabla T| = \left| \frac{\partial T}{\partial x}\vec{i} + \frac{\partial T}{\partial y}\vec{j} + \frac{\partial T}{\partial z}\vec{k} \right| = \sqrt{\left(\frac{\partial T}{\partial x}\right)^2 + \left(\frac{\partial T}{\partial y}\right)^2 + \left(\frac{\partial T}{\partial z}\right)^2}.$$

11. The method of claim 10, wherein assessing the temperature derivative of the thermal field comprises:
determining a contour of the thermal field for a temperature; and
evaluating a component of the gradient vector at one or more locations along the contour.

12. The method of claim 9, wherein the cooling rate is defined as a quantity T', with T' being defined in accordance with $$T' = \frac{\partial T}{\partial t}.$$

13. The method of claim 1, further comprising:
accessing information indicative of an operating range of the manufacturing process;
wherein conducting the plurality of tests comprises conducting tests spanning the operating range of the manufacturing process.

14. The method of claim 1, wherein generating the process map comprises generating a process map based on an interpolation of the temperature derivative.

15. The method of claim 1, wherein the tests comprise one or more experimental tests.

16. The method of claim 1, wherein the tests comprise one or more simulations.

17. The method of claim 1, further comprising:
conducting at least one additional test; and
adjusting the process map based on results of the at least one additional test.

18. The method of claim 1, further comprising:
using the process map to select values of the first and second process variables to yield a selected temperature derivative of the thermal field.

19. The method of claim 1, further comprising:
generating a plurality of process maps characterizing the manufacturing process for forming the structure, each process map corresponding to at least one of a geometry of the structure and a temperature of the structure.

20. The method of claim 19, further comprising:
decomposing a fabrication of another structure into a combination of one or more predetermined structure geometries comprising the predetermined structure geometry; and
controlling the fabrication of the other structure based on the process maps for forming each of the one or more predetermined structure geometries.

21. The method of claim 20, wherein a geometry of the complex structure includes at least one of a height of the other structure and a width of the complex structure.

22. The method of claim 1, wherein the structure comprises a part that is used in the manufacturing process.

23. A system comprising:
one or more processing devices; and
one or more non-transitory computer-readable media storing instructions that are executable by the one or more processing devices to perform operations comprising:
conducting a plurality of tests of an additive manufacturing process, each test conducted at a different combination of at least a first process variable and a second process variable for a structure having a predetermined structure geometry, each test comprising:
locally heating a region of the structure, wherein the local heating results in formation of a thermal field in the structure having the predetermined structure geometry; and
assessing a temperature derivative of the thermal field; and
based on results of the plurality of tests, generating a process map of the temperature derivative of the thermal field for the structure having the predetermined structure geometry, with the temperature derivative based on a function of the first process variable, the second process variable, and the predetermined structure geometry; and
controlling, for the additive manufacturing process, a microstructure formation of a region of a structure having the predetermined structure geometry, the controlling in accordance with the first and second process variables, to generate a thermal gradient in the structure according to the process map.

24. One or more non-transitory computer-readable media storing instructions that are executable by one or more processing devices to perform operations comprising:
conducting a plurality of tests of an additive manufacturing process, each test conducted at a different combination of at least a first process variable and a second process variable for a structure having a predetermined structure geometry, each test comprising:

locally heating a region of the structure to create a melt pool for bonding a first portion of material to a second portion of material, wherein the local heating results in formation of a thermal field in the structure having the predetermined structure geometry; and assessing a temperature derivative of the thermal field;

based on results of the plurality of tests, generating a process map of the temperature derivative of the thermal field for the structure having the predetermined structure geometry, with the temperature derivative based on a function of the first process variable, the second process variable, and the predetermined structure geometry; and controlling, for the additive manufacturing process, a microstructure formation of a region of a structure having the predetermined structure geometry, the controlling in accordance with the first and second process variables, to generate a thermal gradient in the structure according to the process map.

* * * * *

UNITED STATES PATENT AND TRADEMARK OFFICE
CERTIFICATE OF CORRECTION

PATENT NO. : 9,939,394 B2
APPLICATION NO. : 14/422092
DATED : April 10, 2018
INVENTOR(S) : Jack Lee Beuth, Jr. et al.

Page 1 of 1

It is certified that error appears in the above-identified patent and that said Letters Patent is hereby corrected as shown below:

In the Specification

Column 1, Line 19, delete "This invention was made with partial government support under grants CMMI-0700538, CMMI-0700509, CMMI-1131579, and CMMI-1131266 awarded by the National Science Foundation, and under a National Defense Science & Engineering Graduate Fellowship. The government has certain rights in the invention" and insert -- This invention was made with United States government support under CMMI0700509, CMMI0700538, CMMI1131266, and CMMI1131579 awarded by the National Science Foundation. The U.S. government has certain rights in the invention. --

Signed and Sealed this
Thirty-first Day of December, 2024

Derrick Brent
*Acting Director of the United States Patent and Trademark Office*